United States Patent
Reddy et al.

(10) Patent No.: US 11,351,386 B2
(45) Date of Patent: Jun. 7, 2022

(54) SINGLE INCISION SUBCUTANEOUS IMPLANTABLE DEFIBRILLATION SYSTEM

(71) Applicant: CARDIAC PACEMAKERS, INC., St. Paul, MN (US)

(72) Inventors: G. Shantanu Reddy, Minneapolis, MN (US); Andrew L. De Kock, Ham Lake, MN (US)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 220 days.

(21) Appl. No.: 16/104,250

(22) Filed: Aug. 17, 2018

(65) Prior Publication Data
US 2019/0054302 A1   Feb. 21, 2019

Related U.S. Application Data

(60) Provisional application No. 62/546,832, filed on Aug. 17, 2017.

(51) Int. Cl.
| | |
|---|---|
| *A61M 25/01* | (2006.01) |
| *A61N 1/05* | (2006.01) |
| *A61B 17/32* | (2006.01) |
| *A61N 1/375* | (2006.01) |
| *A61N 1/372* | (2006.01) |
| *A61N 1/39* | (2006.01) |
| *A61B 17/00* | (2006.01) |
| *A61B 17/34* | (2006.01) |

(52) U.S. Cl.
CPC ....... *A61N 1/3752* (2013.01); *A61M 25/0194* (2013.01); *A61N 1/0504* (2013.01); *A61N 1/057* (2013.01); *A61N 1/0563* (2013.01); *A61N 1/372* (2013.01); *A61N 1/3956* (2013.01); *A61B 17/3468* (2013.01); *A61B 2017/00946* (2013.01); *A61B 2017/320056* (2013.01); *A61N 2001/058* (2013.01)

(58) Field of Classification Search
CPC ..... A61N 1/0504; A61B 2017/320056; A61M 25/0194
See application file for complete search history.

(56) References Cited

U.S. PATENT DOCUMENTS

| | | |
|---|---|---|
| 4,716,888 A | 1/1988 | Wesner |
| 5,300,106 A | 4/1994 | Dahl et al. |
| | (Continued) | |

OTHER PUBLICATIONS

Darrat et al; "Single Incision Technique for Placement of Subcutaneous Implantable Cardioverter Defibrillators," http://abstractsonline.com/pp8/, accessed May 14, 2018.

(Continued)

*Primary Examiner* — William J Levicky
(74) *Attorney, Agent, or Firm* — Seager, Tufte & Wickhem LLP (57) ABSTRACT

Methods and tool kits for implanting a lead subcutaneously. Examples include tool kits and methods for establishing first and second subcutaneous tunnels at an angle relative to one another to facilitate introduction of a lead to the subcutaneous space. In an example, a tunneling tool and lead assembly are advanced simultaneously into the subcutaneous space. The tunneling tool may include a curved region configured to transition the tool from the first subcutaneous tunnel to the second subcutaneous tunnel with the use of a single incision.

13 Claims, 10 Drawing Sheets

(56) References Cited

U.S. PATENT DOCUMENTS

| | | | |
|---|---|---|---|
| 6,055,457 A * | 4/2000 | Bonner | A61N 1/0563 607/123 |
| 6,647,292 B1 | 11/2003 | Bardy et al. | |
| 6,721,597 B1 | 4/2004 | Bardy et al. | |
| 7,149,575 B2 | 12/2006 | Ostroff et al. | |
| 7,194,302 B2 | 3/2007 | Bardy et al. | |
| 7,299,092 B2 | 11/2007 | Bardy et al. | |
| 7,493,175 B2 | 2/2009 | Cates et al. | |
| 7,655,014 B2 | 2/2010 | Ko et al. | |
| 8,019,443 B2 | 9/2011 | Schleicher et al. | |
| 8,157,813 B2 | 4/2012 | Ko et al. | |
| 8,244,377 B1 | 8/2012 | Pianca et al. | |
| 8,285,397 B2 | 10/2012 | Grandhe | |
| 8,332,043 B1 | 12/2012 | Jaax et al. | |
| 8,532,789 B2 | 9/2013 | Smits | |
| 8,718,793 B2 | 5/2014 | O'Connor | |
| 9,610,435 B2 | 4/2017 | Schleicher et al. | |
| 9,981,121 B2 | 5/2018 | Seifert et al. | |
| 2003/0187460 A1 | 10/2003 | Chin et al. | |
| 2004/0230279 A1 | 11/2004 | Cates et al. | |
| 2006/0004421 A1* | 1/2006 | Bennett | A61N 1/36107 607/41 |
| 2006/0122676 A1 | 6/2006 | Ko et al. | |
| 2008/0208247 A1* | 8/2008 | Rutten | A61N 1/3956 606/205 |
| 2009/0125059 A1 | 5/2009 | Verzal et al. | |
| 2009/0210043 A1 | 8/2009 | Reddy | |
| 2010/0030311 A1 | 2/2010 | Lazeroms et al. | |
| 2010/0125194 A1 | 5/2010 | Bonner et al. | |
| 2011/0054580 A1 | 3/2011 | Desai et al. | |
| 2011/0054581 A1 | 3/2011 | Desai et al. | |
| 2012/0029335 A1 | 2/2012 | Sudam et al. | |
| 2013/0131767 A1 | 5/2013 | Desai et al. | |
| 2014/0144580 A1 | 5/2014 | Desai et al. | |
| 2014/0194963 A1 | 7/2014 | Desai et al. | |
| 2014/0200592 A1 | 7/2014 | O'Connor | |
| 2014/0330248 A1 | 11/2014 | Thompson-Nauman et al. | |
| 2014/0330327 A1 | 11/2014 | Thompson-Nauman et al. | |
| 2015/0105793 A1* | 4/2015 | Cole | A61N 1/3956 606/129 |
| 2015/0133951 A1 | 5/2015 | Seifert et al. | |
| 2015/0209077 A1 | 7/2015 | Marshall | |
| 2015/0343176 A1 | 12/2015 | Aselson et al. | |
| 2015/0352352 A1 | 12/2015 | Soltis et al. | |
| 2016/0339233 A1 | 11/2016 | De Kock et al. | |
| 2017/0020551 A1 | 1/2017 | Reddy et al. | |
| 2017/0021159 A1 | 1/2017 | Reddy et al. | |
| 2017/0095657 A1 | 4/2017 | Reddy et al. | |
| 2017/0100148 A1 | 4/2017 | De Kock et al. | |
| 2017/0319845 A1 | 11/2017 | De Kock et al. | |
| 2017/0319864 A1 | 11/2017 | De Kock et al. | |
| 2018/0036527 A1 | 2/2018 | Reddy et al. | |
| 2018/0036547 A1 | 2/2018 | Reddy | |
| 2018/0133458 A1 | 5/2018 | Foster et al. | |
| 2018/0133462 A1 | 5/2018 | Reddy | |
| 2018/0133463 A1 | 5/2018 | Reddy | |
| 2018/0133494 A1 | 5/2018 | Reddy | |
| 2018/0169384 A1 | 6/2018 | Reddy et al. | |
| 2018/0169425 A1 | 6/2018 | Reddy et al. | |
| 2018/0193060 A1 | 7/2018 | Reddy et al. | |
| 2018/0214686 A1 | 8/2018 | De Kock et al. | |
| 2018/0296824 A1 | 10/2018 | De Kock et al. | |
| 2018/0344200 A1 | 12/2018 | Thakur et al. | |
| 2018/0344252 A1 | 12/2018 | An et al. | |
| 2019/0054289 A1 | 2/2019 | Reddy et al. | |
| 2019/0054290 A1 | 2/2019 | De Kock et al. | |
| 2019/0117959 A1 | 4/2019 | Reddy | |
| 2019/0151651 A1 | 5/2019 | Reddy et al. | |

OTHER PUBLICATIONS

International Search Report and Written Opinion dated Nov. 15, 2018 for International Application No. PCT/US2018/046852.

* cited by examiner

SINGLE INCISION SUBCUTANEOUS IMPLANTABLE DEFIBRILLATION SYSTEM

CROSS REFERENCE TO RELATED APPLICATIONS

The present application claims the benefit of and priority to U.S. Provisional Patent Application Ser. No. 62/546,832, filed on Aug. 17, 2017, the disclosure of which is incorporated herein by reference.

BACKGROUND

The S-ICD System™ from Cameron Health, Inc., and Boston Scientific Corporation presents a new opportunity in cardiac rhythm management to reduce the complications associated with transvenous defibrillator systems. The defibrillator system itself may be implanted subcutaneously without accessing the vasculature or touching the heart.

Figure 1:
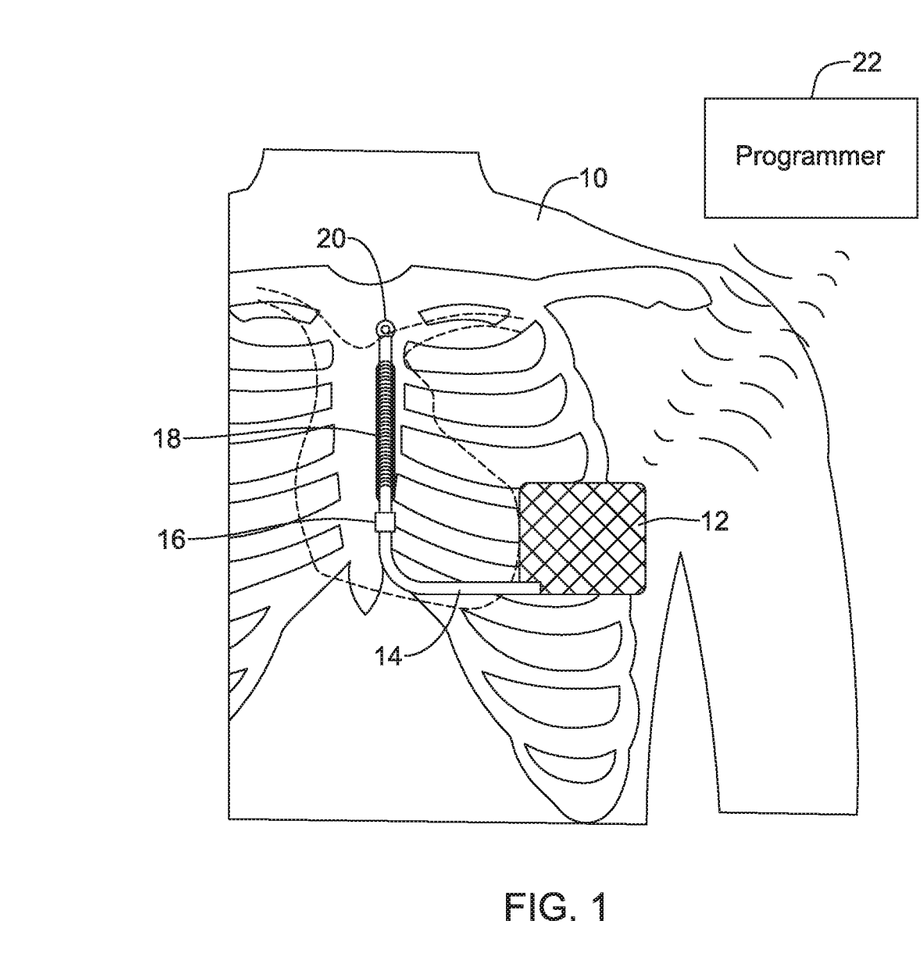
FIG. 1 shows an illustrative subcutaneous-only implantable cardiac stimulus system in an implanted state.
Figure 2:
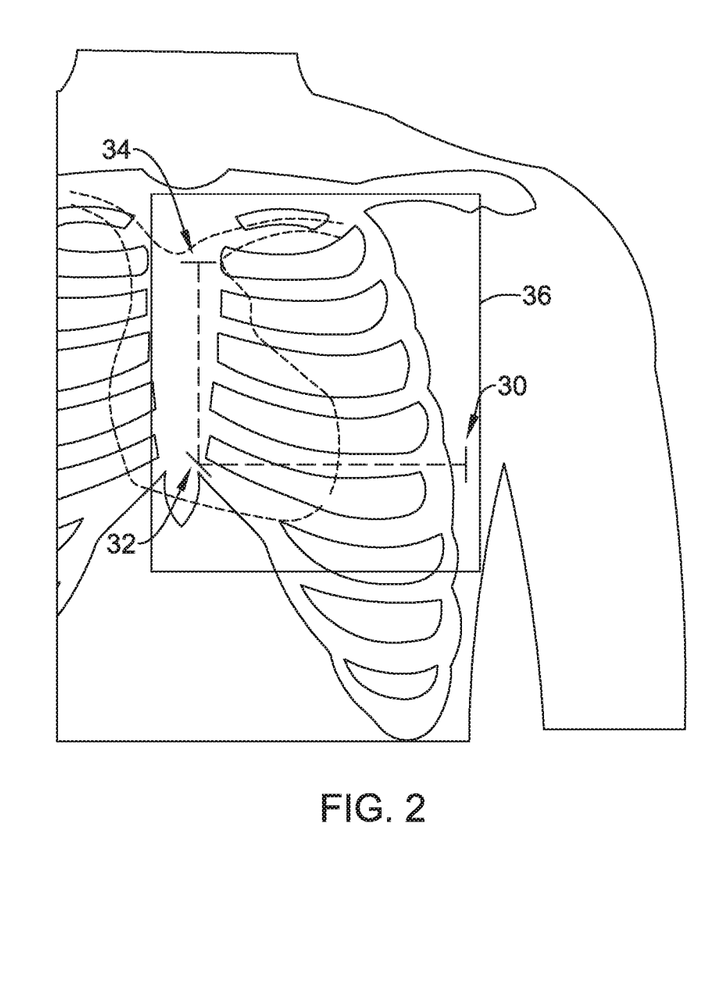
FIG. 2 illustrates certain aspects of the procedure to implant a device as in FIG. 1.

An illustration is provided in FIG. 1. The system is implanted in a patient 10 with a canister 12 in the left axilla at about the level of the cardiac apex. A lead 14 is placed with a first portion extending subcutaneously along the inframammary crease to the xiphoid, and thence superiorly parallel to and 1-2 cm to the left of the sternum. A proximal sense electrode 16, shocking coil electrode 18, and distal tip sense electrode 20 are provided along the parasternal portion of the lead 14. The entire system is implanted outside of the ribcage. As shown in FIG. 2, a typical implant for the S-ICD System uses three incisions 30, 32, 34, and a sterile field represented by shape 36 shown is used to avoid the introduction of microorganisms that can cause infection. Some physicians have also used a two-incision technique foregoing the superior sternal incision 34.

The subcutaneous-only placement prevents some of the more dangerous complications associated with infection, in particular, endocarditis which can result when an infection travels down a transvenous lead into the heart. However, even with reasonable care, some patients may experience infection at the sternal incisions. In addition, some reports have shown that air pockets at either of incisions 32 or 34 can lead to inappropriate shocks within the first few weeks of implantation.

Alternatives to this implantation method are desired that would reduce the number of incisions.

OVERVIEW

The present inventors have recognized, among other things, that a problem to be solved is the inclusion of multiple incision locations in the implantation of a subcutaneous-only defibrillator. A minimally invasive technique and toolset is disclosed herein.

In a first example, a kit for implanting a subcutaneous defibrillation lead in a patient may comprise a tunneling tool and a lead assembly. The tunneling tool may include a handle defining a lumen therein and an elongate shaft having a curved configuration and coupled to and extending distally from the handle. The elongate shaft may define a lumen in fluid communication with the lumen of the handle. The lead assembly may comprise a distal end region including one or more electrodes and one or more fixation elements, a distal dissecting element, such as a cutter cap, coupled to a distal tip of the distal end region, an intermediate region, and a proximal end region including a plug adapted to couple the lead assembly to a defibrillation device. The lead assembly may comprise one or more conductors electrically coupling the one or more electrodes to corresponding contact regions on the plug. The lead assembly may be prepackaged with the tunneling tool such that at least the distal end region and intermediate region thereof may be positioned within the lumen of the handle and the lumen of the elongate shaft, and the distal dissecting element extends distally from a distal end of the elongate shaft.

Alternatively or additionally to any of the examples above, in another example, the curved configuration of the elongate shaft is preformed and fixed.

Alternatively or additionally to any of the examples above, in another example, the curved configuration of the elongate shaft may be adjustable by a user.

Alternatively or additionally to any of the examples above, in another example, the tunneling tool may further comprise a tension knob and compression spring situated at a proximal end of the handle and configured to releasably secure the lead assembly to the tunneling tool.

Alternatively or additionally to any of the examples above, in another example, one or more fixation elements may be self-expanding.

Alternatively or additionally to any of the examples above, in another example, the one or more electrodes may include a distal sense electrode, a proximal sense electrode, and a shocking electrode positioned between the distal and proximal sense electrodes.

Alternatively or additionally to any of the examples above, in another example, the distal dissecting element or cutter cap may function as the distal sense electrode.

Alternatively or additionally to any of the examples above, in another example, the distal dissecting element or cutter cap and the distal sense electrode may form a single monolithic structure.

Alternatively or additionally to any of the examples above, in another example, the one or more fixation elements may include at least a first fixation element adjacent to the distal sense electrode and a second fixation element adjacent to the proximal sense electrode.

Alternatively or additionally to any of the examples above, in another example, the first fixation element and the second fixation element may have a same configuration.

Alternatively or additionally to any of the examples above, in another example, the first fixation element and the second fixation element may each have a differing configuration from the other.

Alternatively or additionally to any of the examples above, in another example, the kit may further comprise a third fixation element positioned between the first fixation element and the second fixation element.

Alternatively or additionally to any of the examples above, in another example, a distal end of the distal dissecting element or cutter cap may have a tapered configuration.

Alternatively or additionally to any of the examples above, in another example, a distal end of the distal dissecting element or cutter cap may have a rounded configuration.

Alternatively or additionally to any of the examples above, in another example, a distal end of the elongate shaft of the tunneling tool may be configured to abut a portion of the distal dissecting element or cutter cap.

In another example, a method of implanting a subcutaneous defibrillation lead in a patient may comprise making a first incision in a lateral location, inserting a tunneling tool and a lead assembly simultaneously into the first incision, tunneling towards the sternum from the lateral incision location, and tunneling generally parallel to the sternum to a desired implant location. The tunneling tool may comprise a handle and a curved elongate shaft having a lumen extending from a proximal end of the tunneling tool to a distal end of the tunneling tool. The lead assembly may be releasably coupled to the tunneling tool and positioned within the lumen thereof and the lead assembly may include a distal dissecting element or cutter cap configured to extend distally beyond the distal end of the tunneling tool.

Alternatively or additionally to any of the examples above, in another example, the method may further comprise after tunneling to the desired implant location, uncoupling the lead assembly from the tunneling tool and proximally retracting the tunneling tool to deploy a first fixation element on the lead assembly.

Alternatively or additionally to any of the examples above, in another example, the method may further comprise fixating the first fixation element to a surrounding tissue.

Alternatively or additionally to any of the examples above, in another example, fixating the first fixation element may comprise applying a proximal pulling force to a proximal end of the lead assembly.

Alternatively or additionally to any of the examples above, in another example, the method may further comprise after fixating the first fixation element proximally retracting the tunneling tool to remove it from the first incision.

Alternatively or additionally to any of the examples above, in another example, proximal retraction of the tunneling tool may deploy at least a second fixation element.

Alternatively or additionally to any of the examples above, in another example, the first and second fixation elements may be self-expanding.

Alternatively or additionally to any of the examples above, in another example, the distal dissecting element or cutter cap may be configured to dissect tissue during tunneling.

Alternatively or additionally to any of the examples above, in another example, a curve of the curved elongate shaft may be preformed and fixed.

Alternatively or additionally to any of the examples above, in another example, a curve of the curved elongate shaft may be manipulatable by a user.

Alternatively or additionally to any of the examples above, in another example, the lead assembly may be releasably secured relative to the tunneling tool via a tension knob and compression spring situated at a proximal end of the handle.

In another example, a method of implanting a subcutaneous defibrillation lead in a patient may comprise making a first incision in a lateral location, inserting a tunneling tool and a lead assembly simultaneously into the first incision, tunneling in a first direction towards the a first location from the lateral incision location with a distal end region of the tunneling tool at a non-orthogonal angle to a target implant configuration, and tunneling in a second direction with the distal end region of the tunneling tool generally parallel to the sternum to a target implant location to position a distal end region of the tunneling tool in a similar configuration to the target implant configuration. The tunneling tool and lead assembly may comprise a handle defining a lumen therein, an elongate shaft coupled to and extending distally from the handle, the elongate shaft defining a lumen in fluid communication with the lumen of the handle. The lead assembly may be positioned within the lumen of the handle and lumen of the elongate shaft and have a distal cutting portion extending distally from a distal end of the elongate shaft and a proximal end portion extending proximally from a proximal end of the handle. One or more fixation elements may be secured to the lead assembly. A curved region of the elongate shaft may transition the tunneling tool from the first direction to the second direction.

Alternatively or additionally to any of the examples above, in another example, the curved region of the elongate shaft may be preformed and fixed.

Alternatively or additionally to any of the examples above, in another example, the curved region of the elongate shaft may be manipulated by a user.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

As explained above, FIG. 1 shows an illustrative subcutaneous-only implantable cardiac stimulus system in an implanted state. FIG. 2 illustrates certain aspects of the procedure to implant a device as in FIG. 1. In this illustration, the procedure for implantation calls for the use of three incisions at locations 30, 32 and 34. To reduce the risk of infection, a sterile field including approximately area 36 may be prepared. This largely tracks the method of implant described in the labeling approved in the United States for the S-ICD® System from Cameron Health and Boston Scientific at the time of commercial approval in 2012. Some illustrative subcutaneous implantable cardiac stimulus systems are described in commonly assigned U.S. Pat. No. 8,718,793, titled ELECTRODE INSERTION TOOLS, LEAD ASSEMBLIES, KITS AND METHODS FOR PLACEMENT OF CARDIAC DEVICE ELECTRODES, U.S. Pat. No. 7,299,092, titled, SUBCUTANEOUS ELECTRODE FOR TRANSTHORACIC CONDUCTION WITH LOW PROFILE INSTALLATION APPENDAGE, and U.S. Pat. No. 7,149,575, titled SUBCUTANEOUS CARDIAC STIMULATOR DEVICE HAVING AN ANTERIORLY POSITIONED ELECTRODE, the disclosures of which are hereby incorporated by reference.

However, in many patients, this sterile field 36 will include various skin folds, for example with obese patients and/or due to proximity to the left breast. It is not always easy to get this area 36 clean for surgery, let alone keeping it clean and dry during the days or weeks after surgery while the incisions 30, 32, 34 all heal. For some patients, the incisions along the sternum may also present aesthetic concerns, for example, because incision 34 may leave a scar that can be visible when wearing ordinary and common clothing and incision 32 may be clearly visible when wearing swimwear.

Reducing the number of incisions has been proposed. Some may use, for example, a two-incision technique similar to that described in some embodiments of U.S. Pat. No. 7,655,014, the disclosure of which is incorporated herein by reference. In this technique, after tunneling between incision 32 and incision 30 and pulling the lead therethrough, an introducer tool having a splittable sheath is advanced from incision 32 toward the manubrium along the sternum, without making incision 34 at all. Next, the introducer tool is removed, leaving the sheath behind, and the lead is introduced through the sheath. Finally the sheath is split and removed over the lead.

The present inventors have identified ways to implant a lead along a subcutaneous path having a curve in the middle of the path as further described below.

Figure 3:
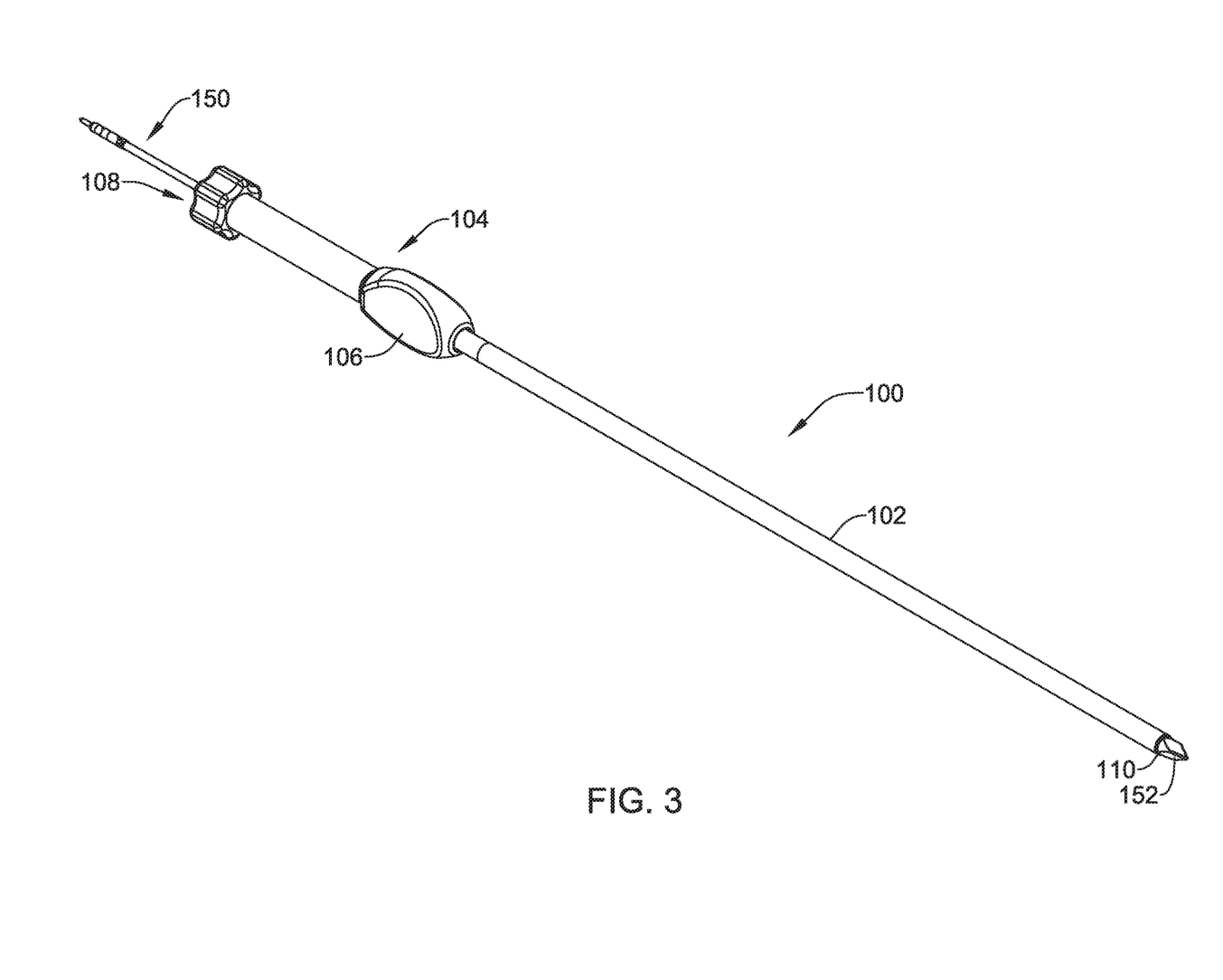
FIG. 3 illustrate a perspective view of an illustrative tunneling tool and lead in a first configuration.

FIG. 3 shows a perspective view of a tunneling tool 100 in a generally straight configuration and including a preloaded lead assembly 150. The tunneling tool 100 includes a shaft 102 coupled to and extending distally from a handle 104. The handle may include a gripping portion 106 and a port 108. The port 108 may be configured to receive the lead assembly 150 therethrough. The lead assembly 150 may extend through the handle 104 and through the shaft 102. In some cases, the lead assembly 150 may extend, at least partially, distally beyond a distal end 110 of the shaft 102. For example, the lead assembly 150 may include a distal dissecting element, shown in the illustrative example as a distal dissecting element, shown as a distal cutter cap 152, positioned at a distal end thereof. The dissecting element or distal cutter cap 152 may be configured to extend distally beyond the distal end 110 of the elongate shaft 102 and to dissect tissue as it is passed through the body. For example, as shown by FIG. 4, below, the distal end 110 of the tunneling tool is generally open to allow the distal tip of the lead assembly 150 to extend through the open distal end thereof.

In the examples shown in the drawings, the distal dissecting element may be a distal cutter cap 152 that takes the form of a slot-head or wedge shape adapted to dissecting layers of tissue. The tip may be blunt; in some examples the tip may be sharp but this may increase the likelihood of cutting fascia or layers, muscle and/or the skin, any of which may be undesirable. Thus a blunt tip is expected to be used in most examples. Rather than a wedge or slot head shape, the distal dissecting element may take the form of a blunt point, such as a "bullet shape" may be used. For example, the distal dissecting element may have a simple rounded geometry. Indeed, it is contemplated that the distal dissecting element may take any form desired to allow for dissection of tissue. A pyramid shape may be used having three, four or more sides, for example, with a blunted point.

Figure 4:
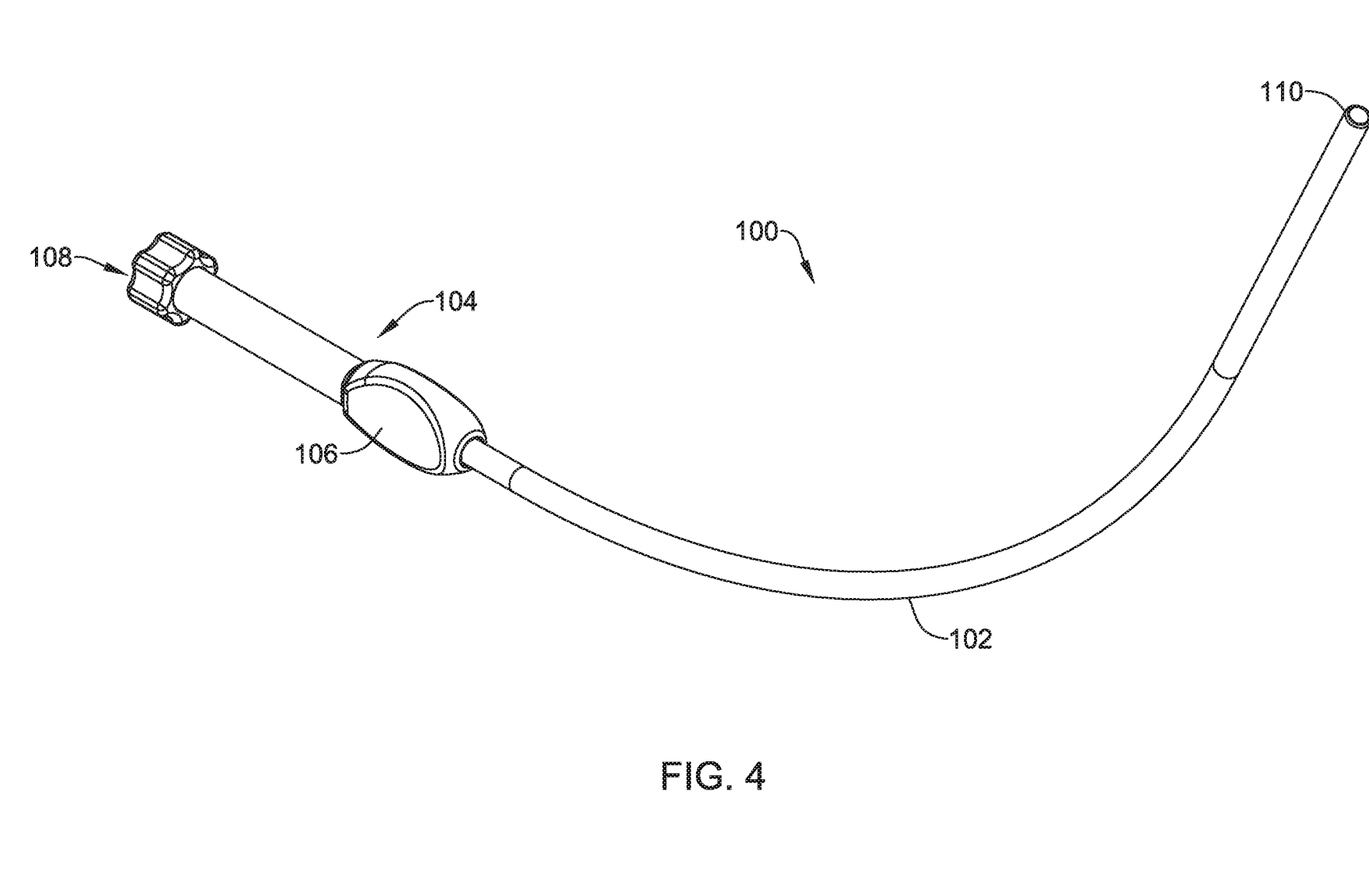
FIG. 4 illustrates a perspective view of the illustrative tunneling tool of FIG. 3 in another illustrative configuration.

FIG. 4 illustrates a perspective view of the tunneling tool 100 in a curved configuration. The elongate shaft 102 of the tunneling tool 100 may be formed from a malleable material such that the physician, or other user, may bend the elongate shaft 102 into a desired configuration. Alternatively, it is contemplated that the tunneling tool 100 may be formed in the curved configuration. For example, the tunneling tool 100 may be formed as a rigid curved structure that resists manual deformation by a physician. In some cases, the elongate shaft 102 may have a large radius of curvature such that the elongate shaft 102 has a gentle, gradual curve over a length thereof. In other cases, the radius of curvature may be smaller such that the elongate shaft 102 has a more abrupt change in direction (e.g., the distal end 110 of the elongate shaft 102 is approximately perpendicular to the handle 104). In some embodiments the elongate shaft 102 may have a radius of curvature in the range of about 2 to 10 centimeters (cm), about 4 to 8 cm or about 6 cm. However, the radius of curvature may be less than 2 cm or greater than 10 cm, as desired.

As can be seen in FIG. 4, the distal tip at 110 of the tunneling tool is open, in order to allow a lead to be placed therethrough. In some examples, the lead to be placed will have a size, length and design to allow the proximal plug on the lead to pass through the interior lumen that extends from the distal end 110 of the tunneling tool to the proximal end 108 by inserting such a plug into the opening at the distal end 110, and passing the lead therethrough, plug first. The tunneling tip (see 152 in FIG. 3) may be sized to prevent the lead form passing all the way through the lumen. It is contemplated that the curved configuration of the tunneling tool 100 may allow a lead, such as lead assembly 150 to be inserted into the subcutaneous tissue using a single incision, as will be described in more detail herein.

Figure 5:
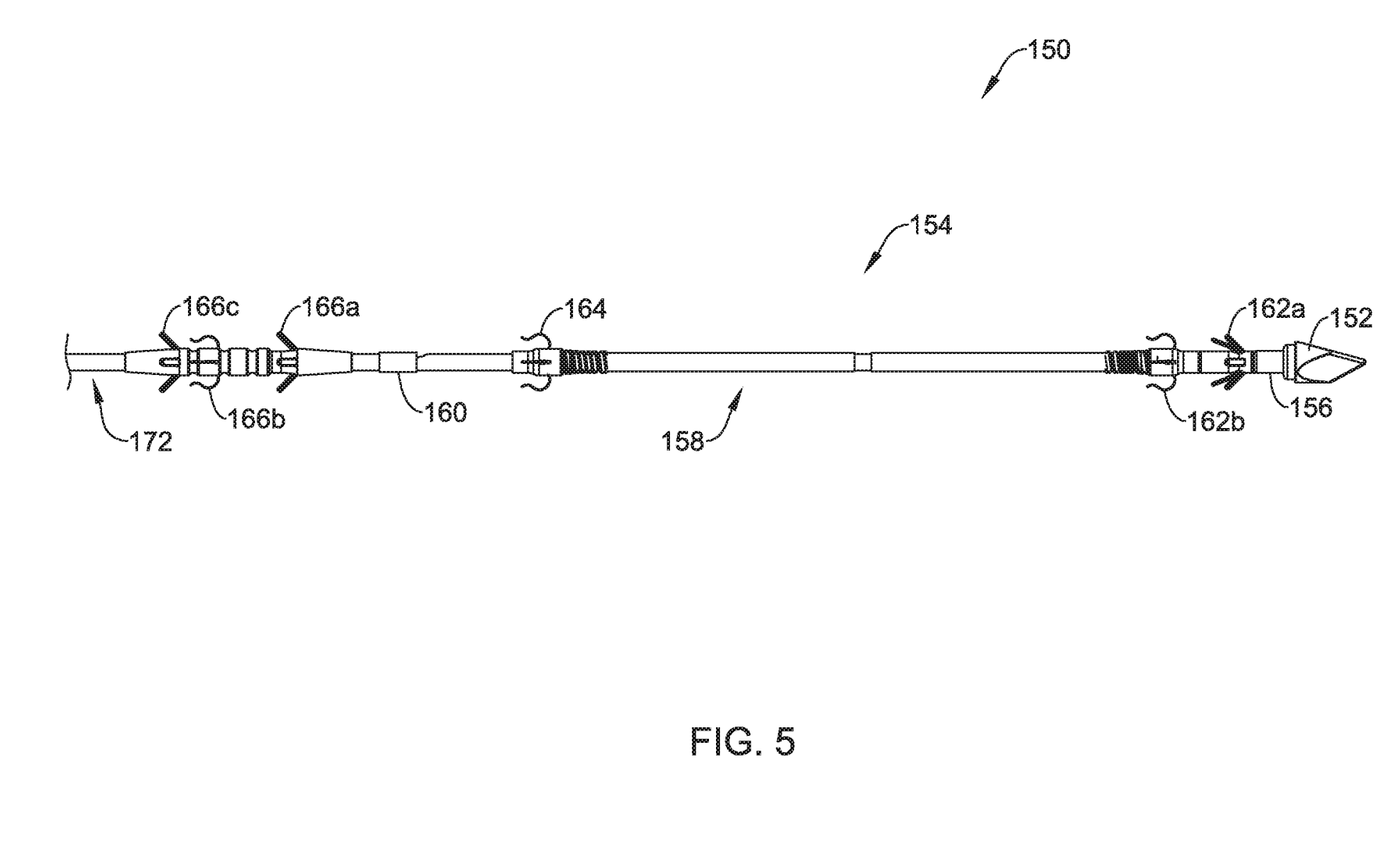
FIG. 5 illustrates a side view of a distal portion of an illustrative lead.

The tunneling tool 100 may be preloaded with a lead assembly 150 prior to tunneling through the subcutaneous tissue. FIG. 5 illustrates a side view of a distal portion 154 of an illustrative lead assembly 150 that may be used with the illustrative tunneling tool 100. As described above, the lead may include a distal cutter cap 152 that serves as a distal dissecting element; other geometries for the distal dissecting element may be used as described above. The distal dissecting element or cutter cap 152 may have a pointed or tapered structure configured to function as a dissecting, separating, or cutting tip for the tunneling tool 100. The dissecting element or distal cutter cap 152 is secured to the lead assembly 150 over or adjacent to the distal electrode 156. This may allow the distal dissecting element or cutter cap 152 to be fixed in place (e.g., the cap 152 is fixed to the lead assembly 150 which in turn is secured to the tunneling tool 100 as described in more detail herein). The dissecting element or distal cutter cap 152 may remain within the body after deployment of the lead assembly 150. In some embodiments, the distal cutter cap 152 may function as the distal sensing electrode. Alternatively, or additionally, the distal dissecting element or cutter cap 152 and the distal electrode 156 may be formed as a single monolithic component.

The distal dissecting element or cutter cap 152 may be formed from a conductive material including, but not limited to, stainless steel. In another example, the distal dissecting element or cutter cap 152 may be separate from the distal electrode 156 and formed of a non-conductive material, if desired. In one example, the distal electrode 156 is entirely formed of the distal dissecting element or cutter cap 152. In one example, the entire lead assembly 150 may be formed of an extruded member of a dielectric material (a polymer for example) that is coextruded onto a core wire that serves as the conductor from the distal electrode 156 to a proximal plug of the lead assembly 150, providing pulling strength and structural integrity to the entire length of the lead assembly.

The distal end region 154 of the lead assembly 150 includes a distal sense electrode 156, a proximal sense electrode 160 and a shocking coil 158 positioned therebetween. The quantity, positioning and/or spacing of the electrodes 156, 158, 160 may be adjusted and/or reconfigured to optimize sensing and/or therapy delivery. For example, both sensing electrodes 156, 160 may be placed proximal to or distal to the coil electrode 158. This is just an example. It is contemplated that the electrodes 156, 158, 160 may be placed beneath the skin and over the ribcage of the patient. In other embodiments, the electrodes 156, 158, 160 may be placed in a substernal location using an implant procedure that may include a xiphoid or sub-xiphoid incision that allows for tunneling along the back side of the sternum. The electrodes 156, 158, 160 may also be placed elsewhere as desired including for example, for use with right sided, anterior-posterior, or other implant positions. Some illustrative discussion of a lead as used in the S-ICD™ System is provided in U.S. Pat. No. 8,483,841; other designs may be used.

In some embodiments, the lead assembly 150 may include one or more fixation elements positioned along a length thereof. The fixation elements may be configured to secure the lead assembly 150 to the tissue without the use of a suture along a distal portion thereof, as the application of a suture would require an additional incision in order to access the lead and underlying tissue.

In some cases, one or more fixation elements 162a, 162b (collectively, 162) may be positioned adjacent to or at the distal sense electrode 156. While the fixation elements 162 are illustrated as having differing structures and/or configurations, it is contemplated that the fixation elements 162 may each have the same structure, as desired. While both fixation elements 162a, 162b are shown for illustrative purposes and may both be included in some examples, other examples include only fixation element 162a (omitting 162b), and still other examples include only fixation element 162b (omitting 162a).

In the example shown another fixation element 164 may be positioned proximal to the shocking electrode 158, although this is not required.

One more fixation elements 166a, 166b, 166c (collectively, 166) may be positioned adjacent to the proximal sense electrode 160. In some instances, the fixation elements 166 may be in the range of 1 to 3 centimeters (cm) proximal to the proximal sense electrode 160. This is just an example, the fixation elements 160 may be positioned closer than 1 cm (proximally), further than 3 cm (proximally, or distal to the proximal sense electrode 160, as desired.

Three fixation elements 166a, 166b, 166c are shown for illustrative purposes and may each be included in some examples. In other examples, any two of the three fixation elements may be included (such as pairing 166a/b, 166a/c, or 166b/c to eliminate one of the three fixation elements). In still other examples, any one of the three fixation elements 166 may be included (such as including only 166a, 166b, or 166c, and omitting the remaining two fixation elements 166a/b/c).

While the fixation elements 166 are illustrated as one 166b having a differing structure and/or configuration from the other two 166a, 166c, it is contemplated that the fixation elements 166 may all have the same structure, differing structures, or combinations thereof, as desired. The structures shown are merely exemplary.

It should be understood than any number of fixation elements 162, 164, 166 in any configuration may be used, as desired. It is contemplated that the configuration of the fixation elements 162, 164, 166 may be selected to stabilize the sensing electrodes 156, 160 and stabilize the shocking electrode 158. In one example, the lead assembly 150 may be provided with a group of fixation elements 162b, 164, 166b. In another example, the lead assembly 150 may be provided with a different group of fixation elements 162a, 164, 166b. In yet another example one of each type it is contemplated that any subset of these groups or the fixation elements 162, 164, 166 shown may be used, including a single fixation element, any two fixation elements, any three fixation elements, etc. Some illustrative fixation element structures are described in U.S. Provisional Patent Application Ser. No. 62/546,867, titled RETENTION MECHANISM FOR AN IMPANTABLE LEAD, and in U.S. Provisional Patent Application Ser. No. 62/547,187, titled FIXATION MECHANISM FOR AN IMPANTABLE LEAD, the disclosures of which are incorporated herein by reference.

The fixation elements 162, 164, 166 may be self-deploying. For example, the fixation elements 162, 164, 166 may be held in a collapsed configuration (not explicitly shown) by the elongate shaft 102 of the tunneling tool or other biasing force. For example, an insertion sheath may be placed over the lead 150 prior to or after loading into the insertion tool. For example, the lead 150 may be loaded in the insertion too, the insertion tool lumen may be flushed with saline or with a lubricating substance, and then an insertion sheath may be slid over the lead 150. Upon removal of the biasing force (for example, proximal retraction of the elongate shaft 102 or tearing away of an insertion sheath), the fixation elements 162, 164, 166 expand such that they engage, push against, and/or anchor in the tissue in which the lead assembly 150 deployed during implantation.

In one example, a shape memory material is used for the fixation elements 162, 164, 166 such a compressed state may be achieved with little tension exerted by the fixation elements until body temperature is reached during implantation. Once implanted and with the elongate shaft 102 removed, the shape memory material can then cause the fixation elements 162, 164, 166 to spring outward, anchoring to the surrounding tissue. In another example, the fixation elements 162, 164, 166 may be formed from other materials including, but not limited to, silicone, polymers, metal, composites, etc.

Figure 6:
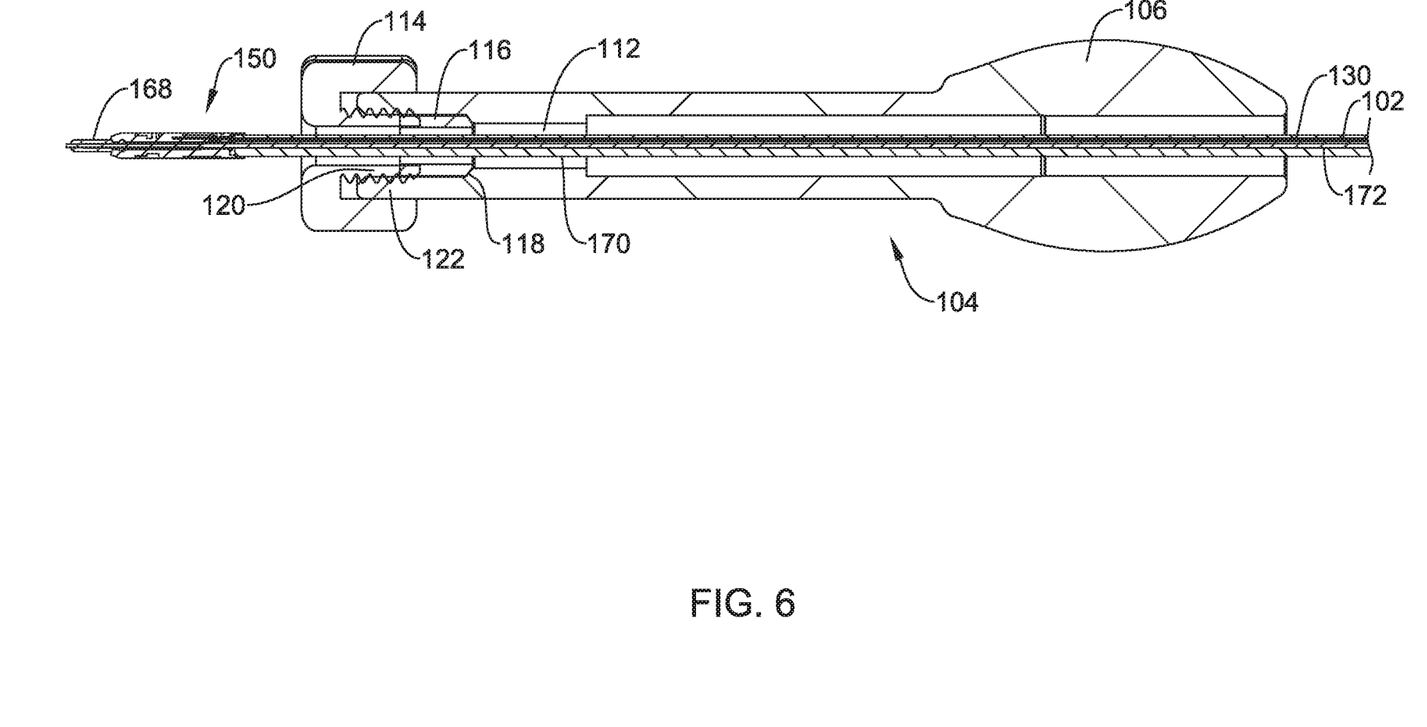
FIG. 6 is a cross-sectional view of a proximal portion of the illustrative tunneling tool and lead.

Referring additionally to FIG. 6, which illustrates a cross-sectional view of a proximal end region of the tunneling tool 100 and the lead assembly 150, the lead assembly 150 may extend proximally through an intermediate region 172 to a proximal end 168 with a proximal pin which along with additional contacts serves in this example as an electrical contact, which may be separated by insulating material, collectively forming a plug for engaging to an implantable pulse generator. The proximal end 168 may further include seal plugs. The pin, contacts, insulating material, and seal plugs may be configured for placement inside a bore on a header of an implantable pulse generator. In some embodiments, the proximal end may have standard plug designs (DF-1, DF-4, etc.). In other examples, the proximal end plug may be selected to be non-standard to prevent use with an implantable pulse generator adapted for transvenous use, which devices typically cannot deliver high enough energy to reliability defibrillate a wide variety of patients if implanted subcutaneously and/or which may be poorly suited to sensing subcutaneous cardiac electrical signals that are of lesser amplitude and wider morphology than those that can be captured with a transvenous, endocardial lead/electrode.

During tunneling it may be desirable to releasably secure the lead assembly 150 to or relative to the tunneling tool 100. This may allow the distal dissecting element or cutter cap 152 of the lead assembly 150 to dissect tissue and/or separate tissue layers during tunneling. The handle 104 may include a lumen 112 from a proximal end to a distal end thereof. The lumen 112 of the handle 104 may be in fluid communication with a lumen 130 of the elongate shaft 102. The lead assembly 150 may extend distally through the lumen 112 of the handle 104 and through the lumen 130 of the elongate shaft 102. The distal dissecting element or cutter cap 152 may extend distally beyond a distal end 110 of the elongate shaft 102.

The handle 104 may include a tension knob 114 coupled to a compression spring 116. The tension knob 114 includes a plurality of threads 120 configured to threadably engage a plurality of threads 122 in the lumen 112 of the handle 104. However, other mechanisms for movably coupling the tension knob 114 and the handle 104 are also contemplated including, but not limited to friction fit, snap fit, etc. The tension knob 114 may be rotated in first direction (e.g., clockwise or counter-clockwise) to distally advance the tension knob 114 and compression spring 116 within the lumen 112. As the compression spring 116 moves distally it contacts a tapered ledge 118 or a smaller diameter region of the lumen 112. The change in diameter 118 may compress the compression spring 116 about an outer surface 170 of the lead assembly 150. The frictional engagement between the compression spring and the outer surface 170 of the lead assembly 150 may reduce or prevent longitudinal and/or rotational movement of the lead assembly 150 relative to the tunneling tool 100. When it is desired to remove the tunneling tool 100 (for example, then the tunneling tool 100 have been advanced to the desired lead assembly 150 deployment location), the tension knob 114 may be rotated in a second direction (e.g., counter-clockwise or clockwise) opposite the first direction. This may cause the tension knob 114 and compression spring 116 to proximally retract. As the compression spring 116 moves proximally it may re-enter the larger diameter region of the lumen 112, expand, and release the compressive force on the outer surface 170 of the lead assembly 150. The tunneling tool 100 may then be proximally retracted to deploy the lead assembly 150.

Figure 7:
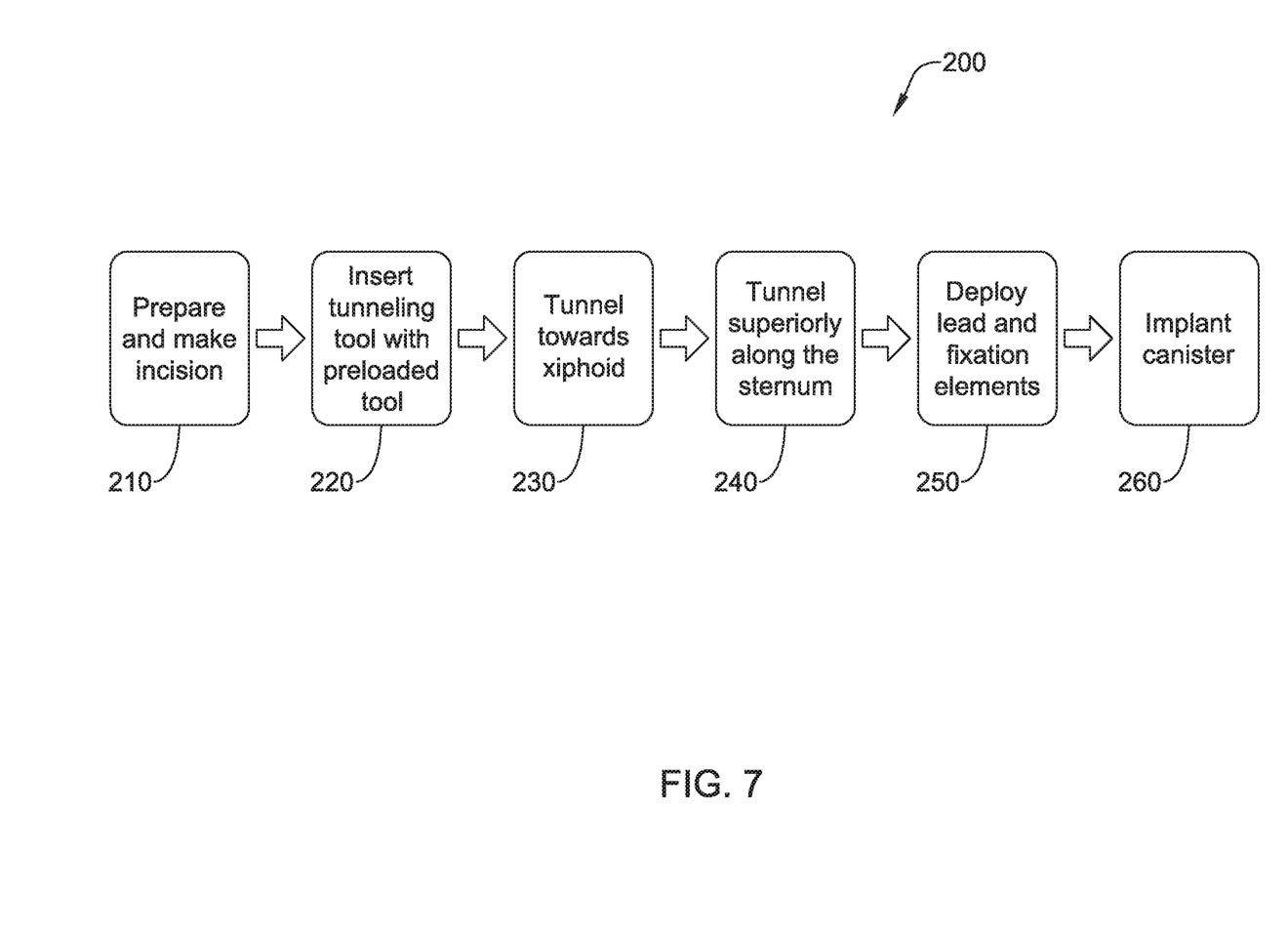
FIG. 7 is a block flow diagram of an illustrative method for implanting a lead for an S-ICD system using a single incision.
Figure 8:
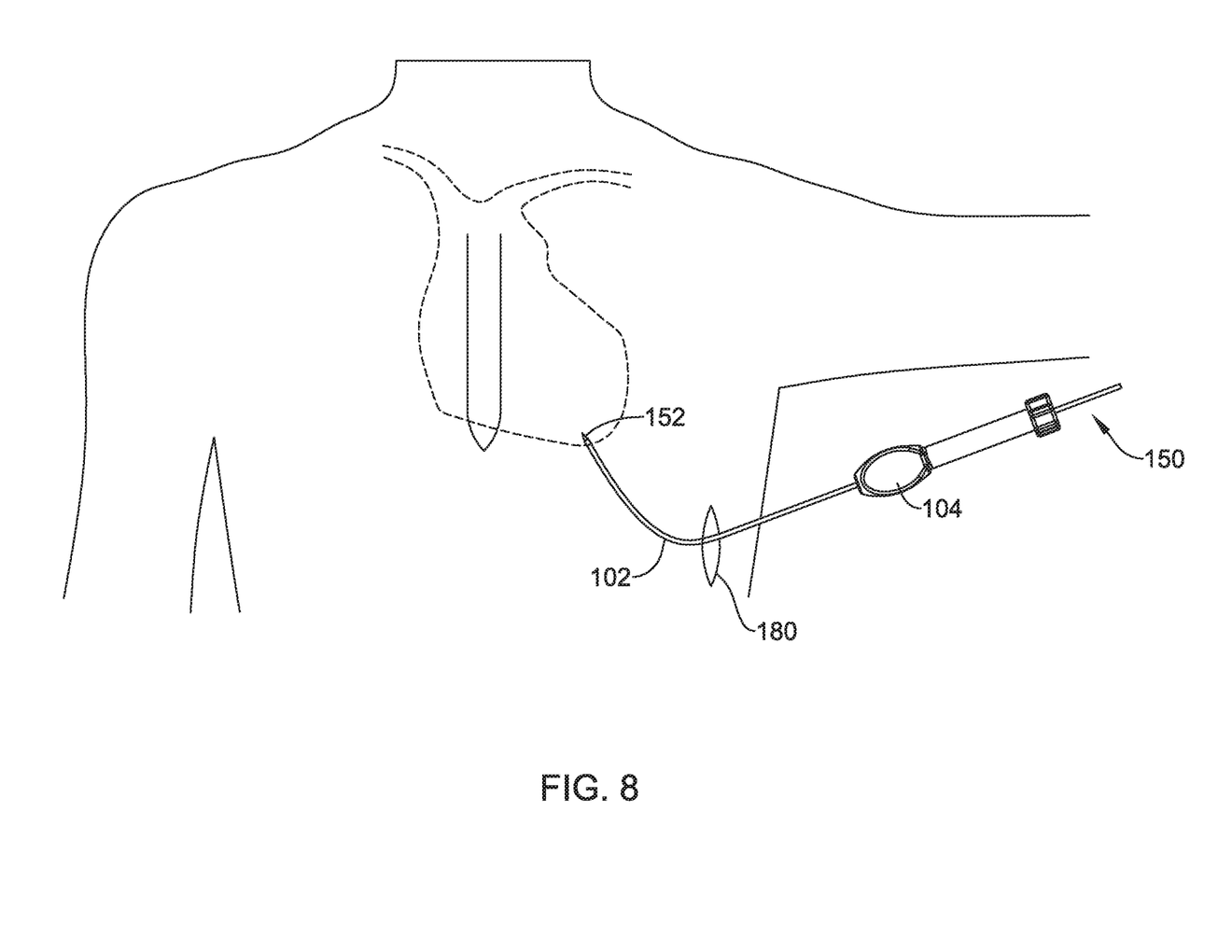
FIGS. 8-9 illustrate the use of a tool set of FIGS. 3 and 4 to implant a lead.
Figure 9:
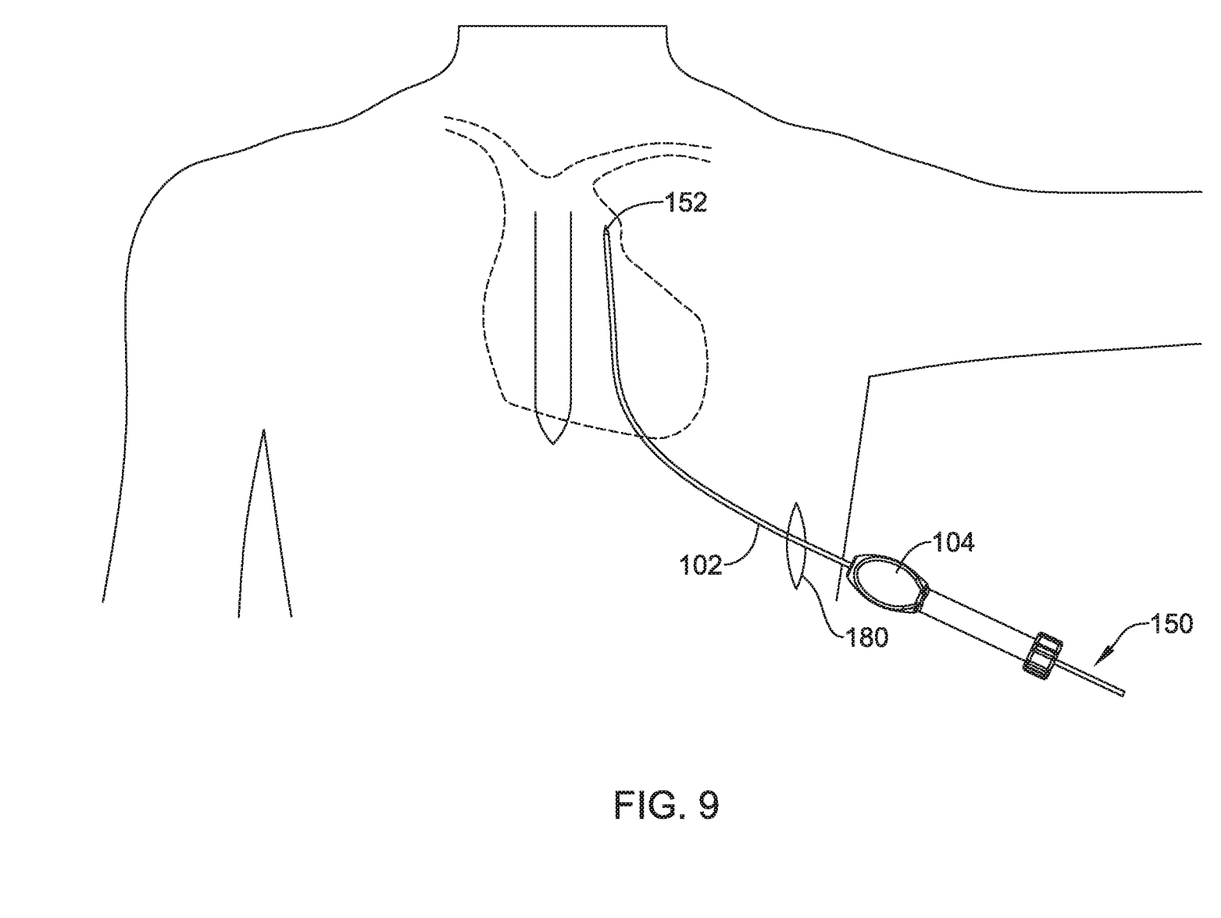
Figure 10:
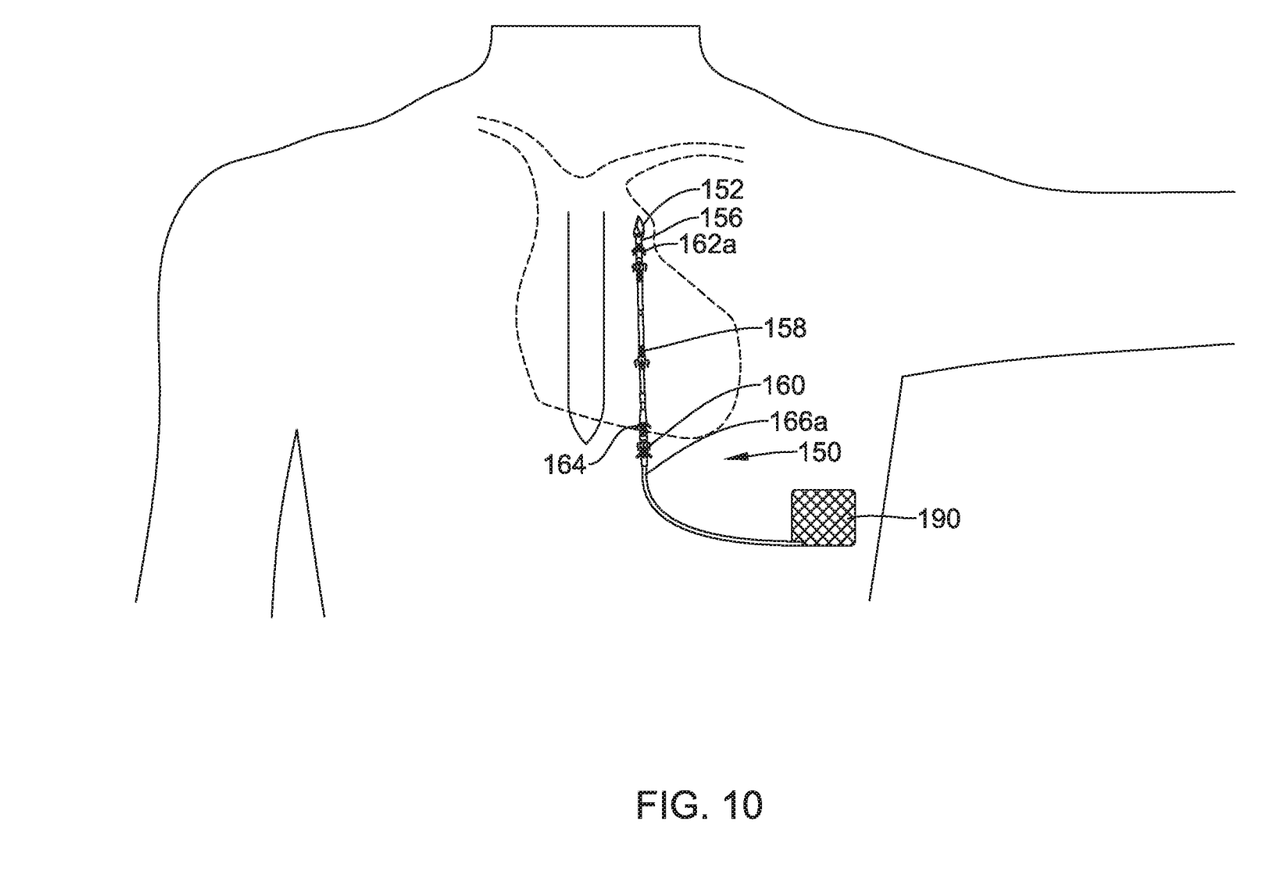
FIG. 10 illustrates an implanted S-ICD system using the method of FIG. 7.

FIG. 7 is a block flow diagram for an illustrative method 200 for implanting a lead with using a pre-loaded lead with a tunneling tool. FIGS. 8-10 illustrate the use of the tunneling tool 100 with a pre-loaded lead assembly 150 to implant a medical device. Starting at block 210, the sterile field is prepared and a first or single incision 180 (see, for example, FIGS. 8 and 9) is made, as shown at 210. The incision 180 may be made near the left axilla. In some cases, the incision 180 may be made at a location inferior to the left axilla. It is contemplated that the incision site 180 may be selected to accommodate the curve of the elongate shaft 102 of the tunneling tool 100. In other words, the incision site 180 may be selected to allow the electrodes 156, 158, 160 to be positioned generally parallel to the sternum in a similar orientation as that of a three incision approach.

Once the incision 180 has been made, the tunneling tool 100 and lead assembly 150 are simultaneously inserted into the tissue, as shown at 220. Step 230 may include tunneling, in some examples, from approximately the left axilla toward the vicinity of the xiphoid (that is, to within about 5 cm, or closer, of the xiphoid). It is contemplated that the tunneling tool 100 and lead assembly 150 may be tunneled towards the sternum at a location superior to the xiphoid. For example, the tunneling tool 100 and lead assembly 150 may be tunneled towards the vicinity of the sternum such that a distal end region of the tunneling tool 100 is at a non-orthogonal angle to a longitudinal axis of the sternum (and/or the final desired configuration of the lead assembly 150), as shown in FIG. 8. As the tunneling tool 100 and lead assembly 150 are tunneled, the distal end 110 of the elongate shaft 102 may press against the distal cuter cap 152 to facilitate tunneling.

Although not required, advancing the tunneling tool 100 and lead assembly 150 at a desired angle may allow the curved elongate shaft 102 to extend generally parallel to the sternum when the tunneling tool 100 and lead assembly 150 are fully advanced (e.g. to allow for a left parasternal position of the lead assembly 150), as shown in FIG. 9. In step 240, as the tunneling tool 100 and lead assembly 150 are further tunneled (e.g., distally advanced) into the subcutaneous space, the curve of the elongate shaft 102 may direct the system to tunnel along the sternum. It is contemplated that the tunneling tool 100 may include additional features configured to facilitate tunneling.

In some illustrative examples, the tunneling tool 100 may include telescoping sections and/or multiple telescoping components. Alternatively, or additionally, the tunneling tool 100 and/or lead assembly 150 may include a steerable and/or powered tip. For example the tunneling tool 100 may comprise pull wires adapted for steering the distal end thereof and/or for reshaping the shaft thereof, with actuators at the proximal handle to aid steering, as illustrated in US PG Patent Application Pub. No. 20170020551A1, titled MINIMALLY INVASIVE METHOD TO IMPLANT A SUBCUTANEOUS ELECTRODE, the disclosure of which is incorporated herein by reference. Other implant tools and methods are disclosed in US PG Patent Application Pub. No. 20170100148, titled DOTTERING TOOLS FOR IMPLANTING MEDICAL DEVICES and US PG Patent Application Pub. No. 20170095657, titled FIXATION DEVICE FOR A SUBCUTANEOUS ELECTRODE, the disclosures of which are incorporated herein by reference.

Once the distal dissecting element or cutter cap 152 is positioned at or near the desired location for the distal sense electrode, the lead assembly 150 may be deployed, as shown at step 250. To deploy the lead assembly 150, the clinician may grasp a proximal end 168 or proximal end region of the lead to maintain its position while proximally retracting the tunneling tool. In other instances, the clinician may palpate for the lead 150 through the skin of the patient and hold the distal tip in place in the body while the tunneling tool 100 is removed. In some cases, the clinician may maintain control of the proximal end region of the lead assembly 150 until at least the distal-most fixation element 162a has been deployed, although this is not required. It is contemplated that an external pushing force may be sufficient to maintain the position of the lead 150 during removal of the tunneling tool 100. Further, as the tunneling tool 100 is proximally retracted, the fixation element(s) 162, 164, 166 deploy into the tissue to hold the lead 150 in place and facilitate fixation of the lead 150 during removal of the tunneling tool 100. The fixation elements 162, 164, 166 also provide acute and/or chronic fixation thereafter. In some cases, a proximal pulling force may be applied to the proximal end region of the lead assembly 150 to further secure the fixation element(s) 162, 164, 166 with the tissue, although this is not required. In such an instance, the distal dissecting element or cutter cap 152 may be advanced distally beyond the target region to accommodate proximal retraction of the lead assembly 150.

It is contemplated that the lead assembly 150 may include enough proximal slack (e.g., a sufficient length extending proximally from the handle 104) to allow at least a portion of the distal end region of the lead assembly 150 to exit the elongate shaft 100 while still allowing the clinician to grip the proximal end region of the lead assembly 150. In some instances, a clinician may apply an external force through the patient's skin to the distal dissecting element or cutter cap 152 (for example, placing a finger or hand on the patient's skin on or above the cap 152). Once at least one fixation element 162, 164, 166 has engaged the clinician may release the proximal end region of the lead assembly 150 and the tunneling tool 100 may be proximally retracted through the incision site 180 and removed from the body, as shown in FIG. 10.

Some examples may include additional features to avoid disturbing lead position during removal of the tunneling tool. In an example, the inner lumen of the tunneling tool may be coated with a highly slippery material, such as a fluoroethylene (ETFE, or PTFE, for example) material to reduce friction and pull on the lead during removal of the tunneling tool. In another example, a biocompatible lubricating substance (such as a silicon oil) may be preloaded in the lumen of the tunneling tool, or on the lead, to reduce friction and pull on the lead during removal of the tunneling tool. In an example, the tunneling tool may include a channel or slot therethrough to allow lateral removal of the lead therefrom. Such a channel may extend from the proximal end, including through the handle 106, of the tunneling tool, to a location 5-10 cm (or more or less) from the distal tip of the tunneling tool, for example. For example, during tunneling an implantation, the lead may be held within the tunneling tool under mild tension between the distal tip (where the dissecting element or cutter cap 152 abuts the distal end of the tunneling tool) and the proximal end region (where the tension knob 114 and associated structure secures the lead). The channel or slot may be placed on the outside portion of the curvature of the tunneling tool, to prevent unintended lateral escape of the lead. In another example, the lead may be held in place inside a tunneling tool having a lateral exit channel along a portion thereof by the use of a splittable insertion sheath, where the channel has a width that would allow the lead to pass therethrough, but not the combination of the lead with a sheath thereon. By splitting the sheath and removing it after desired placement is obtained, the lead would then be free to exit the channel in a lateral manner. In either example, the physician would maintain lead position by holding the proximal end of the lead while the tunneling tool is removed from the patient, such that removal of the elongate tunneling tool does not disturb the lead position. In another example, the tool itself may be splittable. In still another example, the inner diameter of the lumen of the tool may be sized to allow passage over the proximal end of the lead.

Once the lead assembly 150 has been implanted, the canister 190 may be implanted. In some cases, an additional incision may be used for implantation of the canister 190, although this is not required. The lead assembly 150 may be connected to the canister 190 and test operations may be performed. In an example, test operations may be used to verify one or both of device functionality and efficacy. For example, sensing operations may be tested and configured to check for adequate signal availability, for example, or by setting gain, filtering, or sensing vector selection parameters. Defibrillation operations may be tested by inducing an arrhythmia such as a ventricular fibrillation to determine whether the device will sense the arrhythmia and, if the arrhythmia is sensed, to ensure that the device can adequately provide therapy output by delivering defibrillation at a preset energy. Defibrillation testing may include determining for a given patient an appropriate defibrillation threshold, and setting a parameter for therapy delivery at some safety margin above the defibrillation threshold.

The above tools and method may allow for the lead assembly 150 to be implanted using a single incision. This may reduce implant time of an S-ICD system in the range of 40-60% of the time to implant an S-ICD system using a three-incision approach. It is further contemplated that the use of a single incision to implant the lead assembly 150 may reduce infection rates. In some cases, a single incision may improve cosmesis by reducing scars and allowing the scar to be positioned in a relatively discrete location. All of these benefits may alone or in combination improve patient acceptance which is another benefit of a single incision implantable lead.

In some cases, the lead assembly 150 may be delivered using a curved electrode insertion tool (EIT) with a sheath. For example, in contrast to advancing a tunneling tool and lead assembly simultaneously, a tunneling tool may be used to create a tunnel using a single incision prior to advancing a lead. Subsequently, a lead assembly may be implanted using a curved EIT and sheath.

While the above description focuses primarily on a subcutaneous-only implantation, tools such as those described may also be used for a substernal implantation. Substernal implantation may be achieved, for example, by tunneling from a left axillary position to a location near the xiphoid but below the lower rib margin, and proceeding superiorly along the back side of the sternum without penetrating the pericardium or lungs. In addition, rather than a subcutaneous-only implantation, the above described tools and methods may also be used to implant a subcutaneous lead for use with a cardiac device having one or more transvenous or epicardial electrodes/leads. Further, tools and methods such as those described may also be used with two or more incisions.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description.

The Abstract is provided to comply with 37 C.F.R. § 1.72(b), to allow the reader to quickly ascertain the nature of the technical disclosure. It is submitted with the understanding that it will not be used to interpret or limit the scope or meaning of the claims.

Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. A kit for implanting a subcutaneous defibrillation lead in a patient, the kit comprising:
   a tunneling tool having a proximal end and a distal end, comprising:
      a handle defining a lumen therein; and
      an elongate shaft having a curved configuration and coupled to and extending distally from the handle, the elongate shaft defining a lumen in fluid communication with the lumen of the handle; and
   a lead assembly comprising:
      a distal end region including one or more electrodes and one or more fixation elements;
      a distal dissecting element formed of a conductive metal having a wedge shape, coupled to a distal tip of the distal end region;
      an intermediate region; and
      a proximal end region including a plug adapted to couple the lead assembly to a defibrillation device, wherein the lead assembly comprises one or more conductors electrically coupling the one or more electrodes to corresponding contact regions on the plug;
   wherein the lead assembly is prepackaged with the tunneling tool such that at least the distal end region and intermediate region thereof are positioned within the lumen of the handle and the lumen of the elongate shaft, and the distal dissecting element extends distally from a distal end of the elongate shaft such that the distal dissecting element extends distally beyond the distal end of the tunneling tool; and
   wherein the tunneling tool further comprises a tension knob and compression spring situated at a proximal end of the handle and configured to releasably secure the lead assembly to the tunneling tool.

2. The kit of claim 1, wherein the curved configuration of the elongate shaft is preformed and fixed.

3. The kit of claim 1, wherein the curved configuration of the elongate shaft is adjustable by a user.

4. The kit of claim 1, wherein one or more fixation elements are self-expanding.

5. The kit of claim 1, wherein the one or more electrodes includes a distal sense electrode, a proximal sense electrode, and a shocking electrode positioned between the distal and proximal sense electrodes;
   and wherein the one or more fixation elements includes at least a first fixation element adjacent to the distal sense electrode and a second fixation element adjacent to the proximal sense electrode.

6. The kit of claim 5, wherein the first fixation element and the second fixation element have a same configuration.

7. The kit of claim 5, wherein the first fixation element and the second fixation element each have a differing configuration from the other.

8. The kit of claim 1 wherein the one or more electrodes includes a distal sense electrode, and the distal dissecting element functions as the distal sense electrode.

9. The kit of claim 1, wherein the one or more electrodes includes a distal sense electrode, and the distal dissecting element and the distal sense electrode form a single monolithic structure.

10. The kit of claim 1, wherein a distal end of the distal dissecting element has a tapered configuration.

11. The kit of claim 1, wherein a distal end of the distal dissecting element has a rounded configuration.

12. The kit of claim 1, wherein a distal end of the elongate shaft of the tunneling tool is configured to about a portion of the distal dissecting element.

13. The kit of claim 1, wherein the distal dissecting element takes the form of a distal cutting cap having a wedge shape with a blunt distal tip.

* * * * *